US006768799B1

(12) United States Patent
Thomas

(10) Patent No.: US 6,768,799 B1
(45) Date of Patent: Jul. 27, 2004

(54) APPLIANCE INCORPORATING SOUND CANCELLATION SYSTEM

(75) Inventor: John E. Thomas, Des Moines, IA (US)

(73) Assignee: Maytag Corporation, Newton, IA (US)

( * ) Notice: Subject to any disclaimer, the term of this patent is extended or adjusted under 35 U.S.C. 154(b) by 0 days.

(21) Appl. No.: 09/532,447

(22) Filed: Mar. 23, 2000

(51) Int. Cl.[7] ......................... A61F 11/06; G10K 11/16; H03B 29/00

(52) U.S. Cl. ...................................................... 381/71.3

(58) Field of Search .................... 381/71.1, 71.2–71.14, 381/94.1, 94.9

(56) References Cited

U.S. PATENT DOCUMENTS

| | | | | |
|---|---|---|---|---|
| 1,585,218 A | | 5/1926 | Watanabe | |
| 3,147,914 A | | 9/1964 | Hatten et al. | |
| 3,685,610 A | | 8/1972 | Bschorr | |
| 4,427,845 A | * | 1/1984 | Yoshida | 381/94.9 |
| 4,867,284 A | | 9/1989 | Okamura et al. | |
| 5,117,642 A | | 6/1992 | Nakanishi et al. | |
| 5,119,902 A | | 6/1992 | Geddes | |
| 5,125,241 A | | 6/1992 | Nakanishi et al. | |
| 5,127,235 A | | 7/1992 | Nakanishi et al. | |
| 5,203,178 A | | 4/1993 | Shyu | |
| 5,253,486 A | | 10/1993 | Sugahara et al. | |
| 5,319,165 A | | 6/1994 | Geddes | |
| 5,382,134 A | | 1/1995 | Pla et al. | |
| 5,388,956 A | | 2/1995 | Pla et al. | |
| 5,423,658 A | | 6/1995 | Pla et al. | |
| 5,428,965 A | | 7/1995 | Grunwald et al. | |
| 5,448,645 A | | 9/1995 | Guerci | |
| 5,511,127 A | * | 4/1996 | Warnaka | 381/71.1 |
| 5,618,010 A | | 4/1997 | Pla et al. | |
| 5,636,287 A | | 6/1997 | Kubli et al. | |

* cited by examiner

*Primary Examiner*—Minsun Oh Harvey
(74) *Attorney, Agent, or Firm*—Diederiks & Whitelaw, PLC

(57) ABSTRACT

Two electrical power components used in the course of operating an appliance are configured to operate at frequencies which are out-of-phase with respect to one another such that operating noises produced by the first component are effectively reduced in magnitude based on the operation of the second component. The components can be constituted by multiple pumps, a pump/motor combination, a motor and transformer or the like. Operational vibrations can also be reduced by mounting the components in a cabinet of the appliance through a common bracket.

18 Claims, 2 Drawing Sheets

APPLIANCE INCORPORATING SOUND CANCELLATION SYSTEM

BACKGROUND OF THE INVENTION

1. Field of the Invention

The present invention pertains to the art of appliances and, more particularly, to an appliance incorporating a sound cancellation system for quiet operation.

2. Discussion of the Prior Art

When designing an appliance, particularly one slated for use in a household, quiet operation is an extremely appealing characteristic. Actually, considerable attention has been paid in the past to incorporating adequate sound deadening features in various household appliances ranging from dishwashers, refrigerators, laundry machines and the like. Reducing undesirable operational noise levels has been addressed in various ways. For instance, considerable emphasis has been placed on utilizing sound deadening material or insulation in the overall appliance construction. In addition, enhancing the overall sealing arrangement of the appliance has been considered. This is particularly prevalent in reducing the output noise levels in under-the-counter dishwashers wherein it is desirable to create a tight seal between the dishwasher and the adjacent kitchen cabinetry. In laundry machines, a fair amount of sound deadening occurs based on the mounting of the rotatable components. That is, the suspension systems in washers and dryers, as well as the bearing support arrangements, are constructed to minimize potential vibrational and other noises.

Regardless of the fact that various construction and installation requirements have been addressed in attempting to minimize the emission of obtrusive sounds emanating during operation of household appliances, ways to further reduce operational sounds or noises would be desirable. Of course, there have been various proposals for sound canceling systems in other fields. For instance, it has been proposed to incorporate a tunable plate or a speaker unit in certain types of machinery, with the tunable plate or speaker being adapted to emit noise at a frequency which is out of phase with that of another noise producing component of the machine. In general, these types of cancellation systems require the addition of quite expensive, dedicated structure which, at least in the price competitive field of home appliances, would be cost prohibitive.

Based on the above, there exists a need in the art of appliances for a sound cancellation system which is both effective and practical. More specifically, there exists a need for an appliance sound cancellation arrangement which effectively reduces the level of noises generated during operation of the appliance, but which will not represent any significant cost increase for the overall appliance.

SUMMARY OF THE INVENTION

The present invention is directed to the incorporation of a sound cancellation system within an appliance, such as a clothes laundering appliance. In accordance with the invention, multiple power supply components of the appliance are arranged and configured relative to one another such that the sound produced by the operation of one of the components is at least partially canceled by the sound emanating from another one of the components. With this arrangement, at least one of the components performs a standard function associated with the appliance, while another component of the system performs a dual function, with one of the functions being to provide some sort of power used by the appliance for its operation and another of its functions being to cancel out a percentage of the noises developed by the first component.

In accordance with a preferred form of the invention, both the first and second components are constituted by pumps or motors of the appliance, with each of the two components being required in the normal course of operating the appliance. In another preferred embodiment, the second component is defined by a transformer available, not only to reduce the noise produced by the first component, but to run other electrical devices of the appliance. In accordance with the invention, a phase altering device, such as a line capacitor, can be utilized to feed a desired phase into the second component. In any case, the invention is directed to providing a low cost, yet effective, noise cancellation system which advantageously utilizes operational components of an appliance to perform the desired sound cancellation function.

Additional objects, features and advantages of the invention will become more readily apparent from the following detailed description of the invention when taken in conjunction with the drawings wherein like reference numerals refer to corresponding parts in the several views.

DETAILED DESCRIPTION OF THE PREFERRED EMBODIMENTS

Figure 1:
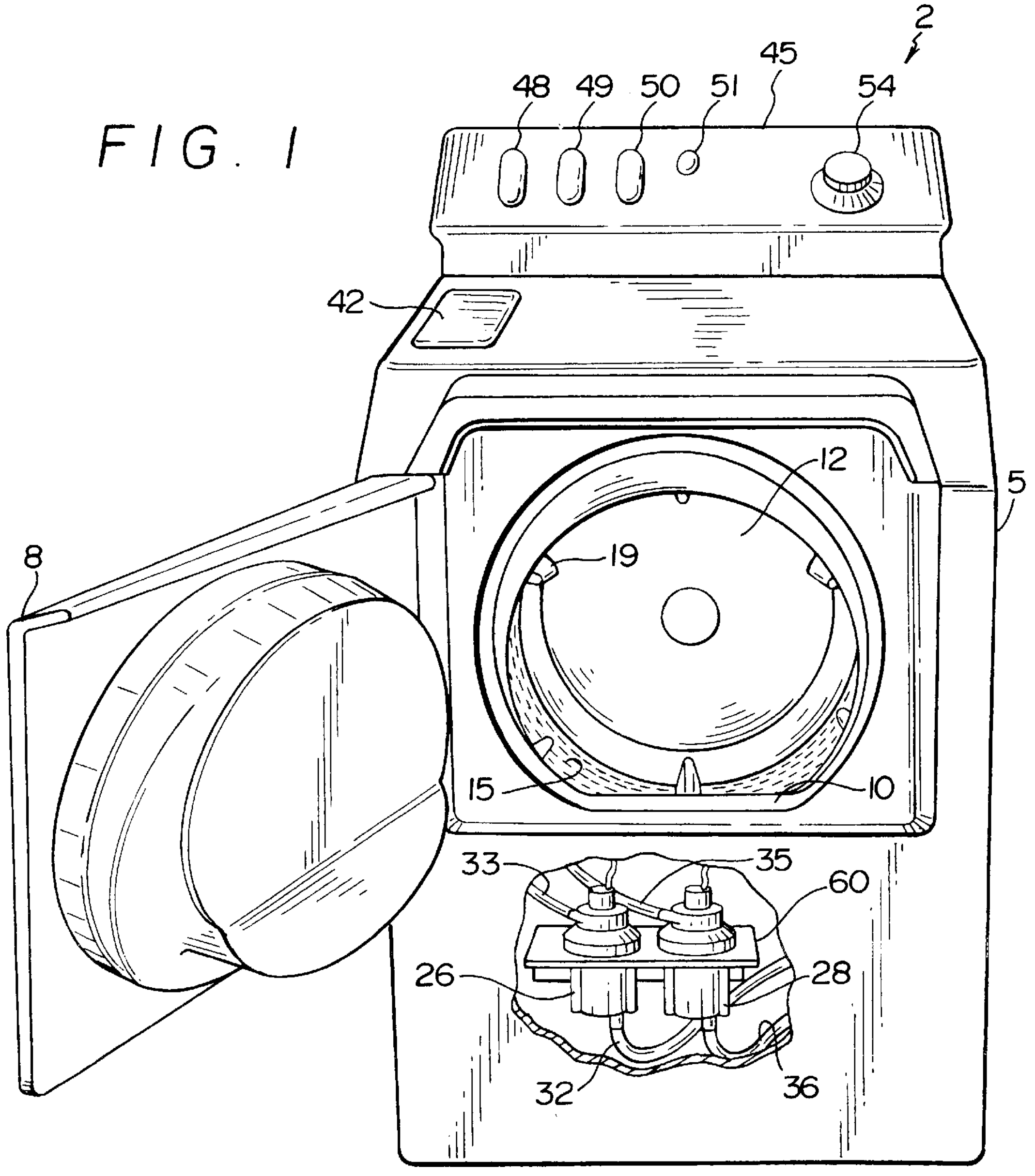
FIG. 1 is a partial broken away view of a horizontal axis washing machine incorporating a sound cancellation system constructed in accordance with the invention.

With initial reference to FIG. 1, an automatic horizontal axis washing machine incorporating the sound cancellation feature of the present invention is generally indicated at 2. In a manner known in the art, washing machine 2 is adapted to be front loaded with articles of clothing to be laundered through a tumble-type washing operation. As shown, automatic washing machine 2 incorporates an outer cabinet shell 5 provided with a front door 8 adapted to extend across an access opening 10. Front door 8 can be selectively pivoted to provide access to an inner tub or spinner 12 that constitutes a washing basket within which the articles of clothing are laundered.

As is known in the art, inner tub 12 is formed with a plurality of holes 15 and multiple, radially inwardly projecting fins or blades 19 are fixedly secured to inner tub 12. Inner tub 12 is mounted for rotation within an outer tub (not shown), which is supported through a suspension mechanism (not shown) within cabinet shell 5 in a manner known in the art. Inner tub 12 is mounted within cabinet shell 5 for rotation about a generally horizontal axis. The rotational axis is actually angled slightly downwardly and rearwardly in the most preferred embodiment. In a manner known in the art, inner tub 12 is rotated during both wash and rinse cycles such that articles of clothing placed therein actually tumble through either water, water/detergent or another washing fluid supplied within inner tub 12. Given that inner tub 12 is provided with at least the plurality of holes 15, the water or water/detergent can flow between the inner and outer tubs. A pumping system, including electric pumps 26 and 28, is provided to control the level of washing fluid within machine 2, with pump 26 particularly controlling the circulation of a water/detergent solution during a laundering operation and pump 28 controlling the timed draining of the fluid from the outer tub (not shown). For this purpose, pumps 26 and 28 are attached to respective sets of inlet and outlet tubes 32, 33 and 35, 36.

The general manner in which the automatic washing machine 2 of FIG. 1 operates is well known in the art and is not considered an aspect of the present invention. Therefore, a complete description of its operation will not be described here. However, for the sake of completeness, automatic washing machine 2 is also shown to include an upper cover 42 that provides access to an area for adding detergent, softeners and the like. In addition, an upper control panel 45, including various selector buttons 48–51 and a control knob 54, is provided for manually establishing a desired washing operation in a manner known in the art.

As shown, pumps 26 and 28 are preferably mounted within cabinet 5 through the use of a common bracket 60. Each pump 26, 28 has an associated operational frequency. During operation, each pump 26, 28 will inherently generate low frequency noise dependent on the line frequency which will typically be at either 60 or 120 Hz. The phase associated with these noises is directly related to the input line phase such that the frequency of these sounds essentially do not vary and can be readily ascertained. In accordance with the present invention, pumps 26 and 28 are set such that pump 28 can operate 180° out of phase with pump 26. In the most basic form, the leads of pump 28 are simply reversed with respect to pump 26 for enabling pump 28 to essentially hum. With this arrangement, pump 28 will generate signals during operation which create a low frequency noise tending to cancel a percentage of the noise generated by the operation of pump 26. Therefore, in essence, pump 28 functions as a transformer/speaker that generates a desired low frequency noise in an inexpensive manner. Since both pumps 26 and 28 are already required for the operation of washing machine 2, the sound cancellation system of the invention advantageously takes advantage of the ability to operate these components in offset phases such that supplemental components dedicated to performing solely a sound canceling function are not required.

Figure 2:
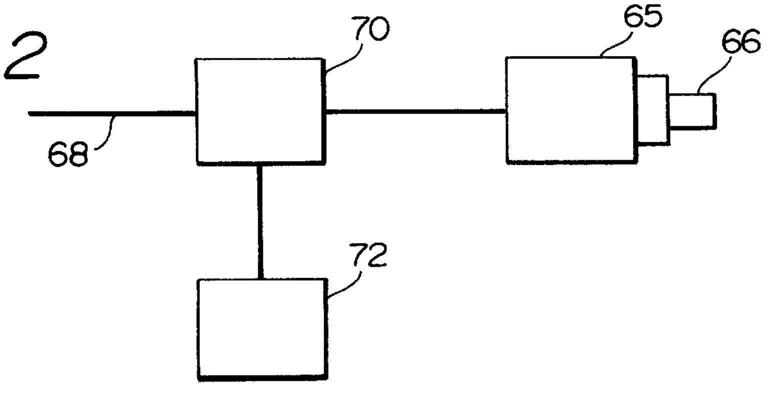
FIG. 2 is a diagram of a second sound cancellation system embodiment for an appliance in accordance with the invention.

It should be readily recognized that the invention can be carried out with other power components in an appliance as well. FIG. 2 schematically represents a motor 65 having an output shaft 66 which can be used to rotate inner tub 12 in a manner known in the art. Motor 65 receives a supply of electricity through power line 68. Arranged in series with motor 65 along power line 68 is a phase altering device 70. In the most preferred form of this embodiment of the invention, phase altering device 70 simply constitutes a line capacitor which functions to feed the proper phase into a transformer 72. Transformer 72 is preferably utilized to run other devices of washing machine 2, such as, for example, lights behind selector buttons 48–51 and/or a lighted skirt around knob 54. In any case, transformer 72 performs a dual function in accordance with the invention similar to that described above with respect to pump 28.

Figure 3:
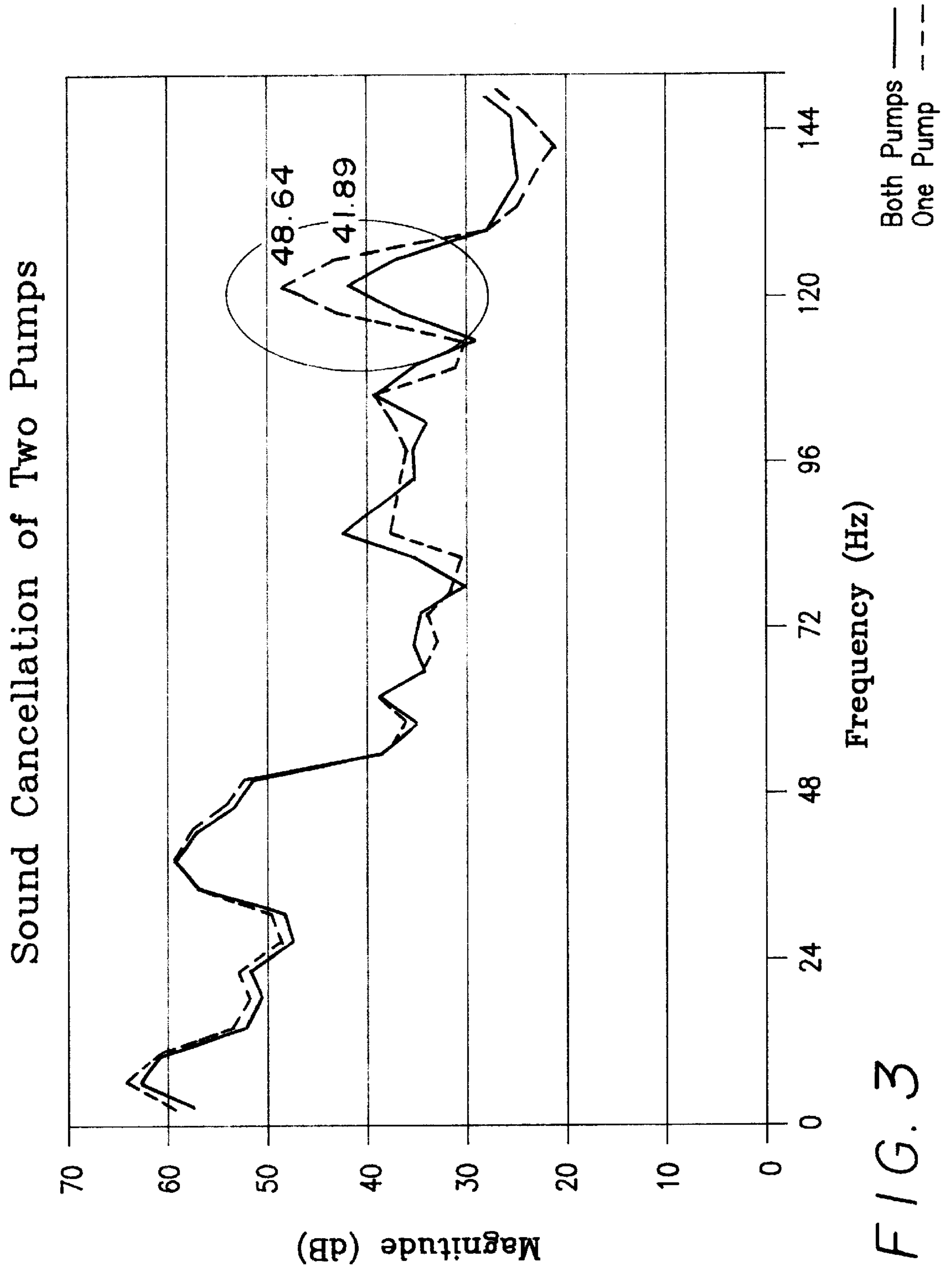
FIG. 3 is graph illustrating the changes in sound output at various operational frequencies for the appliance of FIG. 1.

FIG. 3 is a graph illustrating the operation of pumps 26 and 28 in accordance with the invention. As clearly evident from this graph, at a line frequency of 120 Hz, operating pump 26 alone generates a noise having a magnitude of 48.64 dB. However, also operating pump 28 at this line frequency but out of phase with pump 26 in accordance with the invention, results in an overall operating noise level of 41.89 dB. Therefore, a reduction of 6.75 dB (nearly 10%) can be achieved in accordance with this preferred embodiment of the invention. Since the sound pressure level in decibels (dB) is based on a logarithmic scale, a change of 6.75 dB is actually over 50% quieter. This degree of noise reduction is considered significant and an advantageous characteristic associated with washing machine 2, particularly given that only the manner in which existing components of washing machine 2 are operated is altered in order to achieve this advantageous result. Therefore, the sound cancellation system of the invention adds little to no cost to the overall washing machine 2. A similar advantage is achieved in accordance with the motor/transformer embodiment discussed with reference to FIG. 2. It should also be recognized that corresponding advantages could be obtained utilizing a motor and pump combination. Furthermore, since pumps 26 and 28 are operated out of phase from one another, the vibrations generated during operation will also be out of phase. By mounting pumps 26 and 28 on common bracket 60, the amplitude of the resulting vibrations is greatly diminished. This further reduces the development of associated operational noises.

Although described with respect to preferred embodiments of the invention, it should be readily apparent that various changes and/or modifications can be made to the invention without departing from the spirit thereof. For instance, although the invention has been particularly disclosed with reference to washing machine 2, the invention can also be utilized in various other appliances, including clothes dryers, dishwashers, refrigerators and the like. It is also possible to replace a single pump or motor in an appliance with two smaller pumps/motors which can perform an equal amount of work on a common task but which can operate out of phase from one another to achieve the sound canceling advantages of the invention without requiring the presence of a dedicated sound generating component. In any event, the invention is only intended to be limited by the scope of the following claims.

I claim:

1. An appliance comprising:

a cabinet shell;

a first electrical power component mounted within said cabinet shell, said first power component being required to perform work for operation of the appliance, with the first power component producing a first operating noise having a first frequency and a first volume level; and a second electrical power component mounted within said cabinet shell, with said second power component performing, without using a speaker or sensor, a dual function including a working function required for operation of the appliance, and a sound cancellation function by producing a second operating noise having a second frequency which is configured to be out-of-phase with the first frequency, wherein the first volume level is reduced by the second operating noise and wherein said appliance does not fully function without said second electrical power component.

2. The appliance according to claim 1, wherein the second power component is mounted directly adjacent the first power component within the cabinet shell.

3. The appliance according to claim 2, wherein the first and second power components are secured within the cabinet shell through a common attachment element.

4. The appliance according to claim 1, wherein the first power component constitutes a first pump.

5. The appliance according to claim 4, wherein the second power component constitutes a second pump.

6. The appliance according to claim 5, wherein the first and second pumps are secured to a common mounting bracket.

7. The appliance according to claim 1, wherein the second component constitutes a transformer.

8. The appliance according to claim 7, further comprising a phase altering device electrically connected to the transformer, said phase altering device being electrically interposed between a source of power and the first power component.

9. The appliance according to claim 7, wherein the first power component constitutes an electric motor.

10. The appliance according to claim 7, wherein the transformer further functions to power auxiliary electrical devices of the appliance.

11. The appliance according to claim 1, wherein the second frequency is 180° out-of-phase with the first frequency.

12. The appliance according to claim 1, wherein the appliance comprises a washing machine.

13. The appliance according to claim 1, wherein the second power component is mounted directly adjacent the first power component within the cabinet shell.

14. The appliance according to claim 13, wherein the first and second power components are secured within the cabinet shell through a common attachment element.

15. A method of operating an appliance including a cabinet shell comprising:

placing a first electrical power component in an operational state thereby rotating an element within the cabinet shell of the appliance with the first power component and producing a first operating noise having a first frequency and a first volume level; and reducing the first volume level by activating a second electrical power component which produces, without using a speaker or sensor, a second operating noise having a second frequency which is out-of-phase with the first frequency.

16. The method according the claim 15, further comprising: controlling an operating phase of the second power component through a phase altering device arranged electrically in series with each of the first and second power components.

17. The method according to claim 15, wherein the second power component is operated 180° out-of-phase with the first frequency.

18. A method of operating an appliance including a cabinet shell comprising:

placing a first electrical power component in an operational state thereby producing a first operating noise having a first frequency and a first volume level;

reducing the first volume level by activating a second electrical power component which produces, without using a speaker or sensor, a second operating noise having a second frequency which is out-of-phase with the first frequency; and controlling first and second fluid flows through the first and second power components respectively.

* * * * *